(12) United States Patent
Wilson et al.

(10) Patent No.: US 7,894,058 B2
(45) Date of Patent: Feb. 22, 2011

(54) SINGLE-LENS COMPUTED TOMOGRAPHY IMAGING SPECTROMETER AND METHOD OF CAPTURING SPATIAL AND SPECTRAL INFORMATION

(75) Inventors: Daniel W. Wilson, Montrose, CA (US); William R. Johnson, Brea, CA (US); Gregory H. Bearman, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/352,576

(22) Filed: Jan. 12, 2009

(65) Prior Publication Data
US 2009/0180115 A1 Jul. 16, 2009

Related U.S. Application Data

(60) Provisional application No. 61/010,826, filed on Jan. 11, 2008.

(51) Int. Cl.
*G01J 3/28* (2006.01)

(52) U.S. Cl. .................................... 356/328

(58) Field of Classification Search .............. 356/328
See application file for complete search history.

(56) References Cited

U.S. PATENT DOCUMENTS

| | | |
|---|---|---|
| 5,159,199 A | 10/1992 | LeBaw |
| 5,760,899 A | 6/1998 | Eismann |
| 6,104,488 A | 8/2000 | LeVan |
| 6,522,403 B2 | 2/2003 | Wilson et al. |
| 7,092,088 B2 | 8/2006 | Schau |
| 2002/0175286 A1 | 11/2002 | Murguia |
| 2006/0050391 A1 | 3/2006 | Backlund et al. |
| 2006/0158645 A1 | 7/2006 | Maier et al. |
| 2006/0170920 A1* | 8/2006 | Granger ............... 356/328 |
| 2006/0252070 A1 | 11/2006 | Boege et al. |
| 2006/0274308 A1 | 12/2006 | Brady et al. |

OTHER PUBLICATIONS

Hartke et al., "Hyperspectral-dual spectral region imaging spectrometer," *Proceedings of SPIE*, vol. 5563, pp. 156-166, 2004.
Johnson et al., "All-reflective snapshot hyperspectral imager for ultraviolet and infrared applications," *Optics Letters*, vol. 30, No. 12, Jun. 15, 2005, pp. 1464-1466.
Hartke et al., "Non-scanning dual infrared band hyperspectral imaging spectrometer design," *Proceedings of SPIE*, vol. 6295, 12 pages, (2006).
Johnson et al., "Spatial-spectral modulating snapshot hyperspectral imager," *Applied Optics*, vol. 45, No. 9, Mar. 20, 2006, pp. 1898-1908.

* cited by examiner

*Primary Examiner*—Gregory J Toatley
*Assistant Examiner*—Abdullahi Nur
(74) *Attorney, Agent, or Firm*—Christie, Parker & Hale, LLP (57) ABSTRACT

Computed tomography imaging spectrometers ("CTISs") employing a single lens are provided. The CTISs may be either transmissive or reflective, and the single lens is either configured to transmit and receive uncollimated light (in transmissive systems), or is configured to reflect and receive uncollimated light (in reflective systems). An exemplary transmissive CTIS includes a focal plane array detector, a single lens configured to transmit and receive uncollimated light, a two-dimensional grating, and a field stop aperture. An exemplary reflective CTIS includes a focal plane array detector, a single mirror configured to reflect and receive uncollimated light, a two-dimensional grating, and a field stop aperture.

19 Claims, 12 Drawing Sheets

SINGLE-LENS COMPUTED TOMOGRAPHY IMAGING SPECTROMETER AND METHOD OF CAPTURING SPATIAL AND SPECTRAL INFORMATION

CROSS-REFERENCE TO RELATED APPLICATION(S)

This application claims priority to and the benefit of U.S. Provisional Patent Application 61/010,826, titled SINGLE-LENS COMPUTED TOMOGRAPHY IMAGING SPECTROMETER, filed on Jan. 11, 2008, in the United States Patent and Trademark Office, the entire content of which is incorporated herein by reference.

STATEMENT REGARDING FEDERALLY SPONSORED RESEARCH OR DEVELOPMENT

The invention described herein was made in the performance of work under a NASA contract, and is subject to the provisions of Public Law 96-517 (35 U.S.C. §202) in which the Contractor has elected to retain title.

FIELD OF THE INVENTION

The invention is directed to computed tomography imaging spectrometers and to methods of capturing spatial and spectral information. More particularly, the invention is directed to computed tomography imaging spectrometers having a single lens.

BACKGROUND OF THE INVENTION

Current imaging spectrometer systems are generally either slit imaging spectrometers or bandpass-filter imaging spectrometers. However, slit imaging spectrometers must scan the scene spatially to build up a 2D image, and bandpass-filter imaging spectrometers must scan the scene spectrally. In contrast, computed tomography imaging spectrometers ("CTISs") enable spectral imaging of transient events by capturing spatial and spectral information in a single snapshot. That is, CTISs capture spatial and spectral information from a two-dimensional ("2D") scene in a single image frame. Spectra are obtained by means of tomographic reconstruction.

Figure 1:
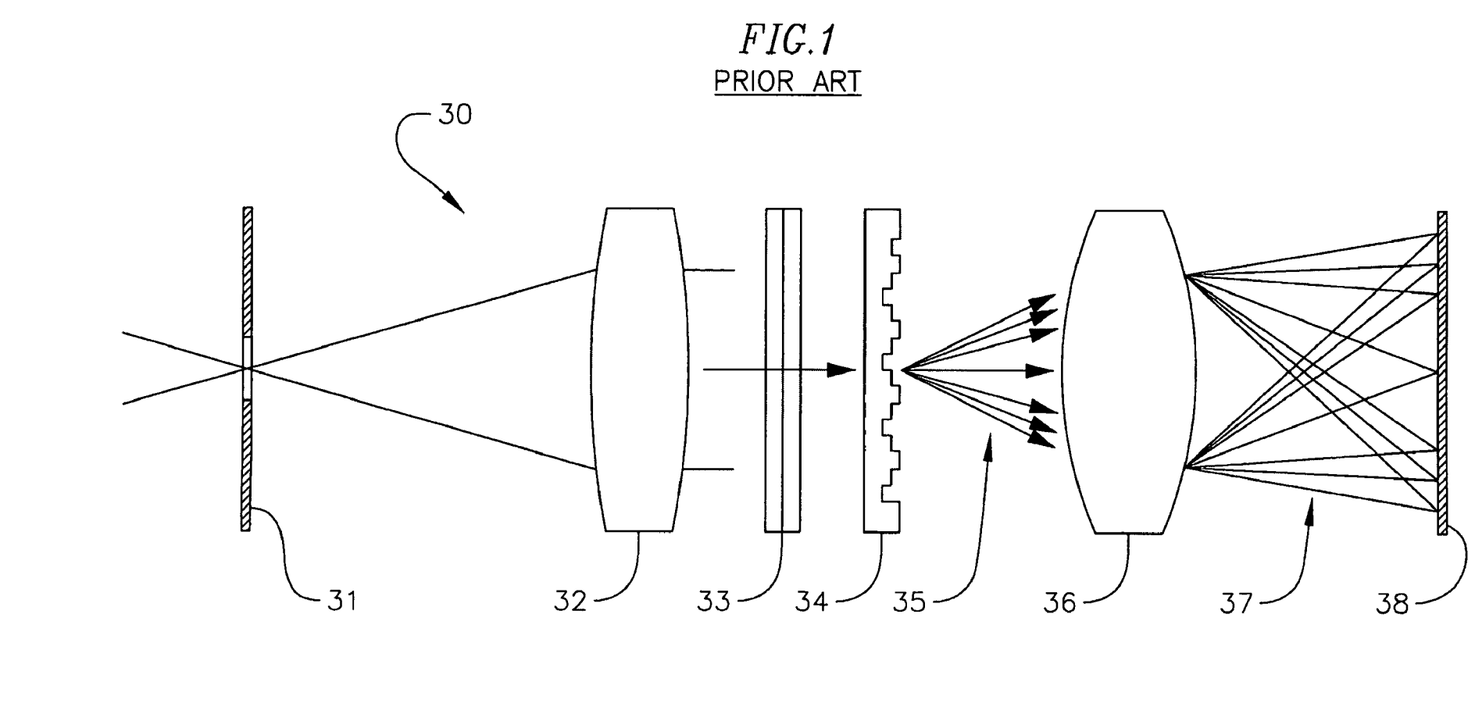
FIG. 1 is an optical layout of a prior art CTIS system.

In a typical transmissive CTIS 30, as shown in FIG. 1, spots of light passing through a field stop 31 are collimated in a collimating lens 32, filtered through a wide-band filter 33, and passed through a 2D grating 34 which produces a 2D array of diffraction orders 35. A final focusing element, such as a re-imaging lens 36, re-images the various diffraction orders of light 37 onto a focal plane array ("FPA") detector 38, e.g. a charge coupled device ("CCD"), that records the intensity of the incident light. Reflective-type CTISs operate in much the same manner except that a collimating mirror is used in place of the collimating lens.

Each diffraction order of light 37 transmitted from the grating 34 produces a spectrally dispersed image of the scene, except for the undiffracted "zeroth" order which produces an undispersed image in the center area of the FPA detector 38. The CTIS captures the scene's spatial and spectral information by imaging the scene through a 2D grating disperser. This produces multiple, spectrally dispersed images of the scene that are recorded by a focal plane array ("FPA") detector. From the captured intensity pattern, computed-tomography algorithms can be used to reconstruct the scene into a cube of spatial (x and y) and spectral (wavelength) information.

The CTIS enables transient-event imaging spectrometry for applications including, for example: 1) spectral imaging of living biological systems that move/change rapidly during an experiment (e.g. cells, retina, colon, etc.); 2) industrial processes such as semiconductor etching; or 3) defense surveillance on regions in which neither the location nor the time of an explosion, missile launch, or chem-bio weapon deployment is known.

Current CTIS systems typically utilize a long focal-length collimation lens and a short focal-length re-imaging lens. The collimation lens is heavy, thereby significantly contributing to the total weight of the system. Further, the mechanical coupling of the collimation lens and the re-imaging lens adds weight away from the body. In addition, the use of both a collimation lens and a re-imaging lens presents issues associated with magnification, and the need to re-focus the re-imaging lens presents issues associated with calibration.

SUMMARY OF THE INVENTION

In one embodiment of the present invention, an imaging spectrometer for capturing spatial and spectral information from an object scene includes a focal plane array detector, a single lens configured to transmit and receive uncollimated light, a two-dimensional grating, and a field stop aperture. The single lens may be a macro lens that permits close-focusing to enable positioning of the field stop aperture close to the lens. The single lens may be configured to receive light from the grating or transmit light to the grating. The focal plane array detector may include a digital image sensor, and may be a monochrome detector or a color detector.

The single lens may be any lens suitable to image the field stop aperture onto the focal plane array detector. The specifications of the lens depend on the distance from the field stop to the lens/grating plane and from that plane to the focal plane array detector. The lens may include multiple glass elements to minimize aberrations over the spectral band of operation, but residual aberrations are acceptable because they are calibrated during construction and corrected during tomographic reconstruction. The lens may also have an f-number of between one and two to maximize the light throughput and minimize the distance from the field-stop aperture to the focal-plane array detector, but the lens is not limited to such an f-number.

In another embodiment of the present invention, an imaging spectrometer for capturing spatial and spectral information from an object scene includes a focal plane array detector, a two-dimensional grating, a single mirror assembly configured to reflect and receive uncollimated light, and a field stop aperture. The focal plane array detector may be an infrared detector. The concave mirror may be configured to focus uncollimated light onto the focal plane array detector.

In another embodiment of the present invention, a method of capturing spatial and spectral information from an object scene includes forming an image of the object scene on a field stop aperture, passing uncollimated light through the field stop aperture, dispersing the uncollimated light with a two-dimensional grating, wherein the two-dimensional grating produces a two dimensional array of uncollimated diffraction orders of light, focusing the uncollimated diffraction orders of light onto a focal plane array detector using a single lens or mirror, and recording the intensity of the light incident on the focal plane array detector.

In another embodiment of the present invention, a method of capturing spatial and spectral information from an object scene includes forming an image of the object scene on a field stop aperture, passing uncollimated light through the field stop aperture to a single lens or mirror, passing the uncollimated light through the single lens to a two-dimensional grating, dispersing the uncollimated light with the two-dimensional grating, wherein the two-dimensional grating produces a two dimensional array of uncollimated diffraction orders of light and passes the uncollimated diffraction orders of light onto a focal plane array detector, and recording the intensity of the light incident on the focal plane array detector.

BRIEF DESCRIPTION OF THE DRAWINGS

These and other features and advantages of the present invention will be better understood by reference to the following detailed description when considered in conjunction with the accompanying drawings in which.

DETAILED DESCRIPTION OF THE INVENTION

Computed tomography imaging spectrometers ("CTISs") operate by multiplexing the spectral and spatial data of an image onto a focal plane, which captures all the information in a single snapshot. This feature allows video rate spectral imaging. Spectra are obtained by means of tomographic reconstruction. As discussed above, current CTISs employ two lenses, one for collimating incident light, and one for re-imaging the collimated light. These two-lens systems are heavy and expensive to manufacture. According to an embodiment of the present invention, however, the weight and cost of CTISs are reduced by a system employing a single lens instead of the conventional collimation lens and re-imaging lens.

Transmissive CTIS

Figure 2:
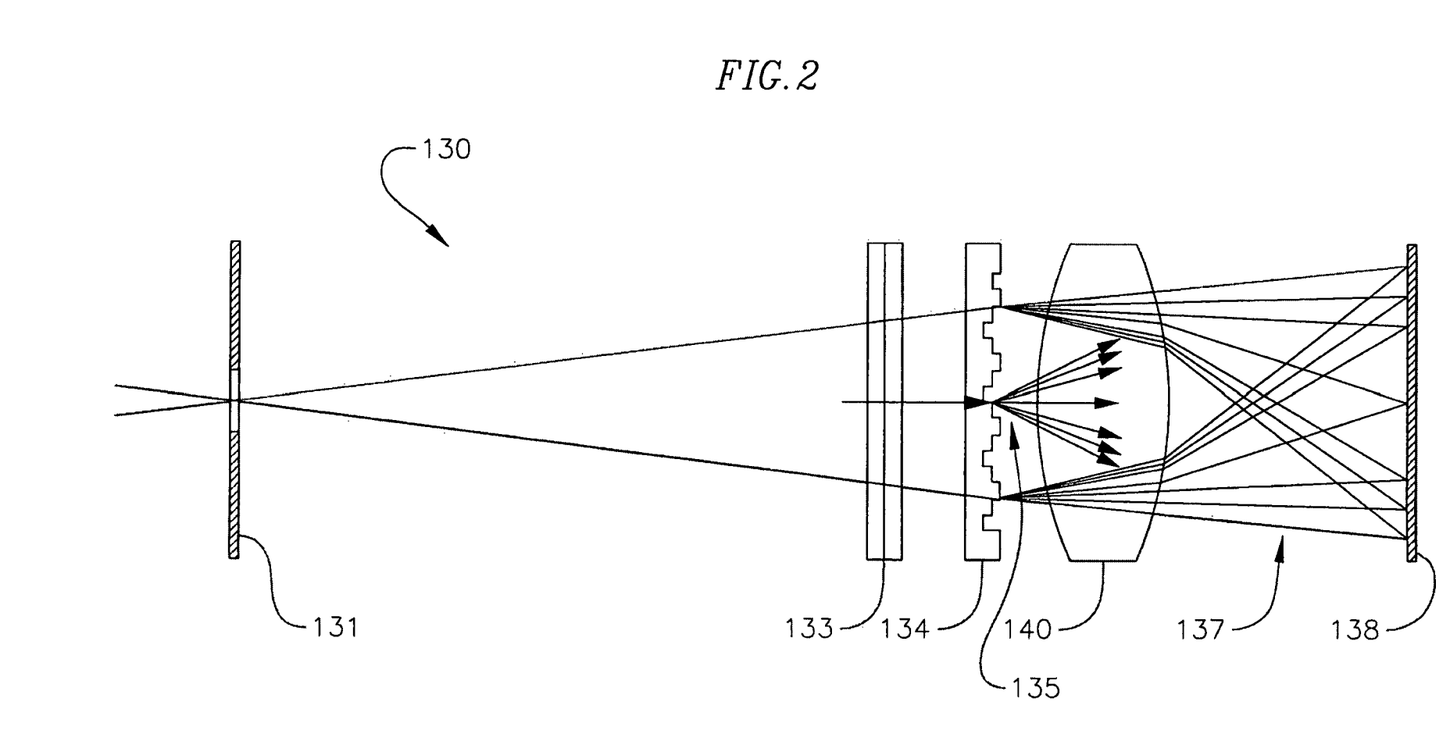
FIG. 2 is an optical layout of a CTIS system according to an embodiment of the present invention.

In an embodiment of the present invention as shown in FIG. 2, a transmissive CTIS 130 generally includes a 2D grating 134, a lens 140, and an FPA detector 138. The CTIS 130 may further include at least one filter 133 through which the incident light is passed through before reaching the grating 134. The lens 140 according to embodiments of the present invention may be any suitable lens, such as a macro lens, capable of focusing on the field stop at the desired distance. In one embodiment, for example, the lens is stronger than either the conventional collimating lens or the conventional re-imaging lens. The specifications of the lens depend on the distance from the field stop to the lens/grating plane and from that plane to the focal plane array detector. The lens may include multiple glass elements to minimize aberrations over the spectral band of operation, but residual aberrations are acceptable because they are calibrated during construction and corrected during tomographic reconstruction. The lens may also have an f-number of between one and two to maximize the light throughput and minimize the distance from the field-stop aperture to the focal-plane array detector, but the lens is not limited to such an f-number. In another embodiment of the present invention, the lens 140 is similar in size to a conventional re-imaging lens, but has a shorter focal length. The lens is configured to image the field stop aperture onto the focal plane array detector, preferably with minimal aberration. The distances from the field stop to the lens/grating, d1, and from the lens/grating to the detector, d2, may be chosen to achieve the desired magnification, M=d2/d1, of the field stop aperture. The desired size of the field stop aperture typically depends on the optics that image the scene onto the field stop (which frequently fixed by the application, e.g. a microscope for microscopy, a fundus scope for retinal imaging, or a particular lens for general imaging).

Figure 2A:
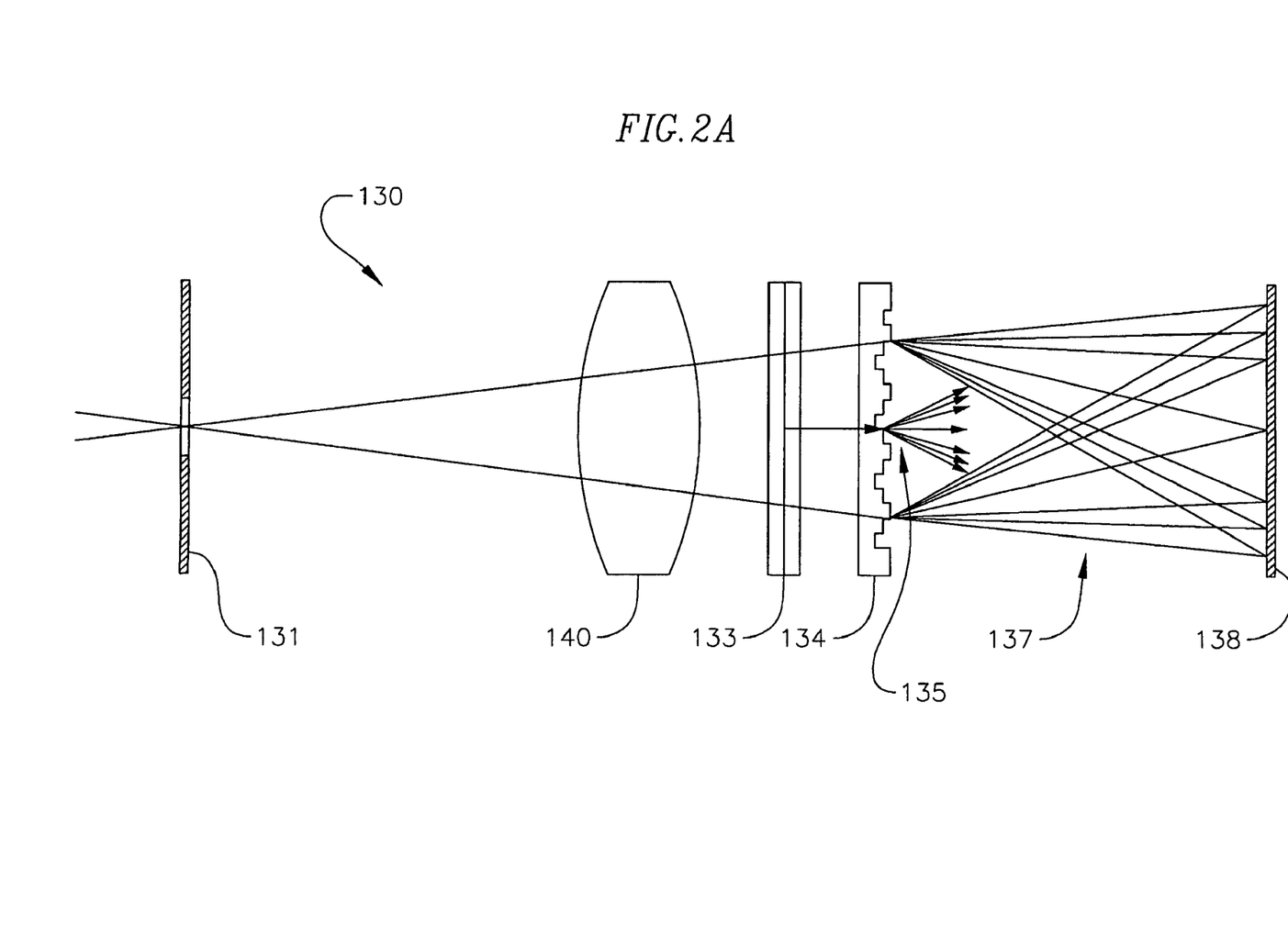
FIG. 2A is an optical layout of a CTIS system according to another embodiment of the present invention.
Figure 2B:
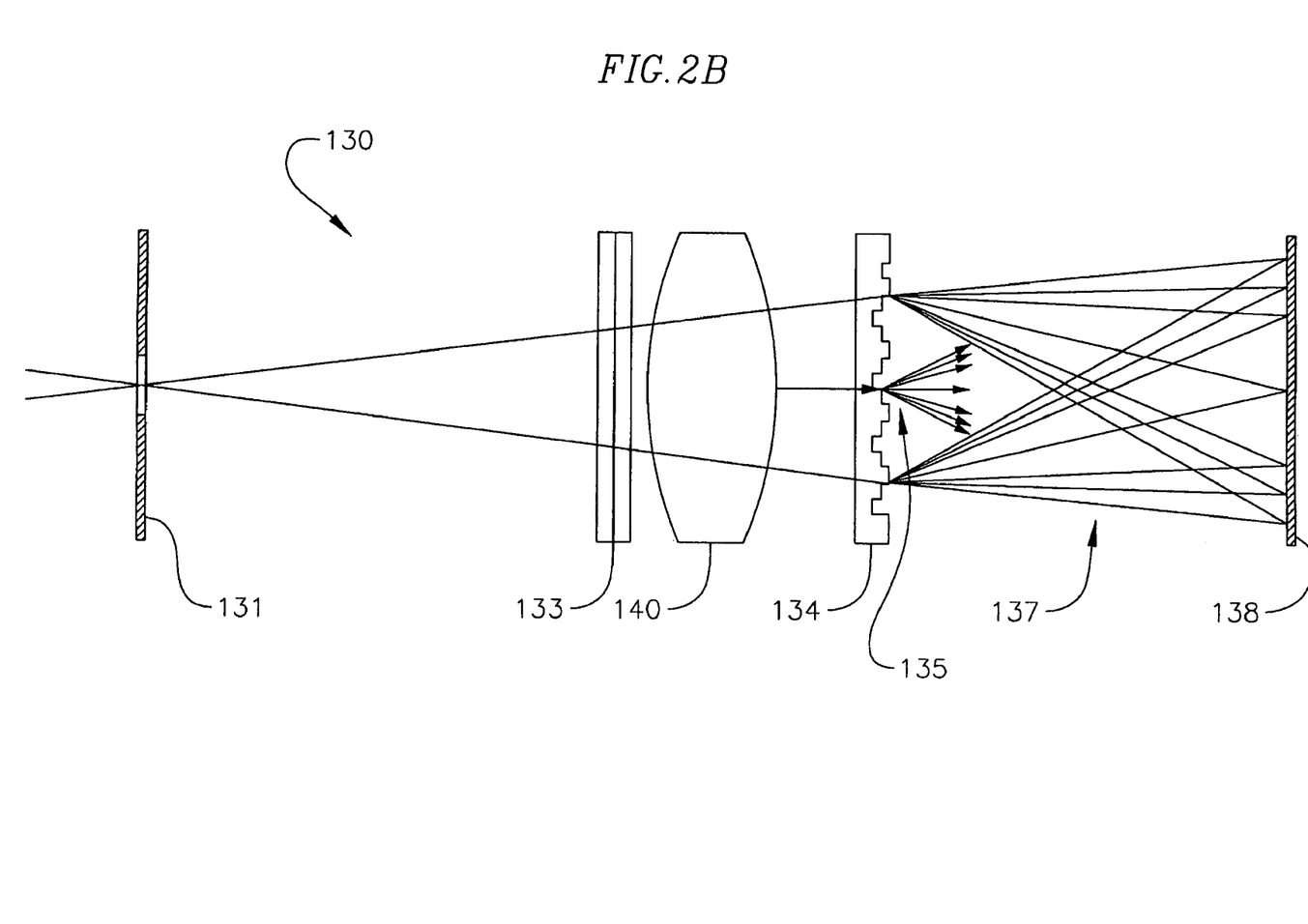
FIG. 2B is an optical layout of a CTIS system according to yet another embodiment of the present invention.
Figure 2C:
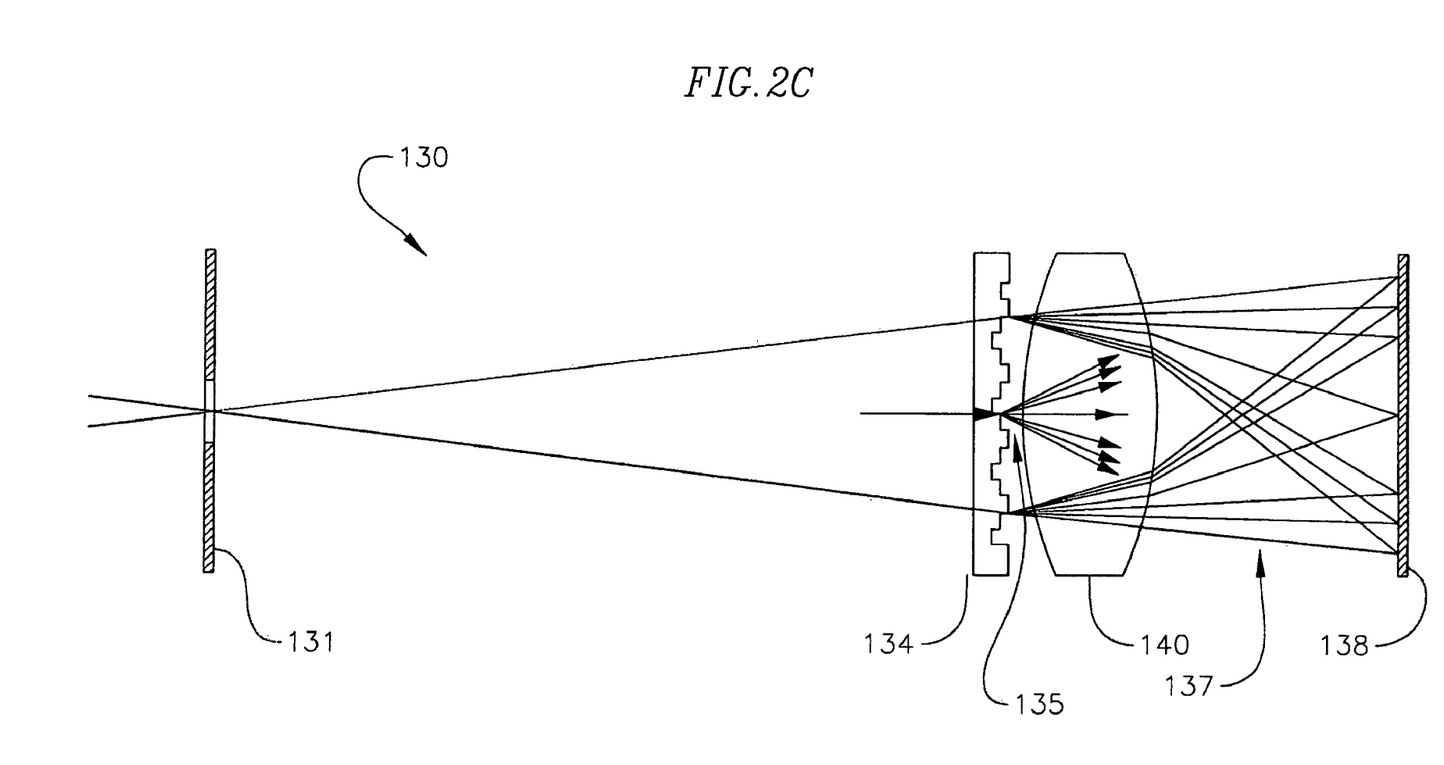
FIG. 2C is an optical layout of a CTIS system according to still another embodiment of the present invention.

In some embodiments of the present invention, as shown in FIG. 2, the lens 140 may be positioned between the grating 134 and the FPA detector 138. In other embodiments, as shown in FIG. 2A, the lens 140 may be positioned between the field stop 131 and the filter 133. In still other embodiments, as shown in FIG. 2B, the lens 140 may be positioned between the filter 133 and the grating 134. In embodiments in which no filter is used, as shown in FIG. 2C, the lens 140 may be positioned between the field stop 131 and the grating 134, or, as shown in FIG. 2D, between the FPA detector and the grating.

The grating 34 can be any suitable grating for diffracting the incident light. In one embodiment, for example, the grating 34 is a surface-relief computer-generated hologram exhibiting a transmitted phase shift that varies with the inverse cosine of the angle of incidence. Because cos(6)= 0.994, there will be negligible change to the diffraction efficiencies of the orders (dispersed images). Nonlimiting examples of suitable gratings are described generally in U.S. patent application Ser. No. 11/638,036 to Wilson, et al., filed Dec. 12, 2006, the entire content of which is incorporated herein by reference.

The FPA detector 138 can take a number of forms, such as a color FPA detector. For example, in one embodiment, the color FPA detector may comprise a digital color camera including a digital image sensor, such as a Foveon X3® digital image sensor or a Bayer color filter mosaic. The Foveon X3® digital image sensor includes three layers of pixels (i.e. one red layer, one blue layer and one green layer) on top of each other embedded in a silicon sensor. The Bayer color filter mosaic includes a single layer of a repeating array of red, green and blue filter material deposited on top of each spatial location, and the Bayer color filter mosaic uses twice as many green filters as red or blue filters. In another embodiment, the color FPA detector may include three charge coupled devices ('CCDs'), one for each color: red, green and blue.

In still another embodiment, the FPA detector may comprise any suitable device, such as a monochrome camera or a color camera for use with a color camera CTIS, over which is positioned a transmission filter that performs a user-defined transmissive function. For example, a color filter adapted to transmit a single color (e.g. red, green or blue) can be positioned over the FPA detector.

The total mass of the CTISs according to embodiments of the present invention is lower than the mass of conventional CTISs. The inventive CTISs employ a single lens, eliminating the added weight and complexity associated with conventional two-lens systems. The inventive, single-lens systems are less expensive to produce and output spatial and spectral information of the same or better quality than conventional two-lens systems. Also, because the entire lens assembly of the inventive systems is attached to the FPA detector, tilts, rotations, and defocusing of the collimating lens, that deteriorate the quality of the output, are eliminated.

In conventional CTISs, such as the one shown in FIG. 1, the collimation lens 32 is typically chosen to have a long focal length, e.g. greater than about 100 mm, to provide de-magnification of the field stop 31. Further, the grating 34 diameter is typically about 20 mm in diameter, which results in a collimation lens 32 effective f-number greater than about 5. However, according to embodiments of the present invention, as shown in FIG. 2, a single lens 140 is used in place of both the collimation lens and the re-imaging lens. As a result, the maximum angle of incidence on the grating is less than about 6 degrees.

Figure 3:
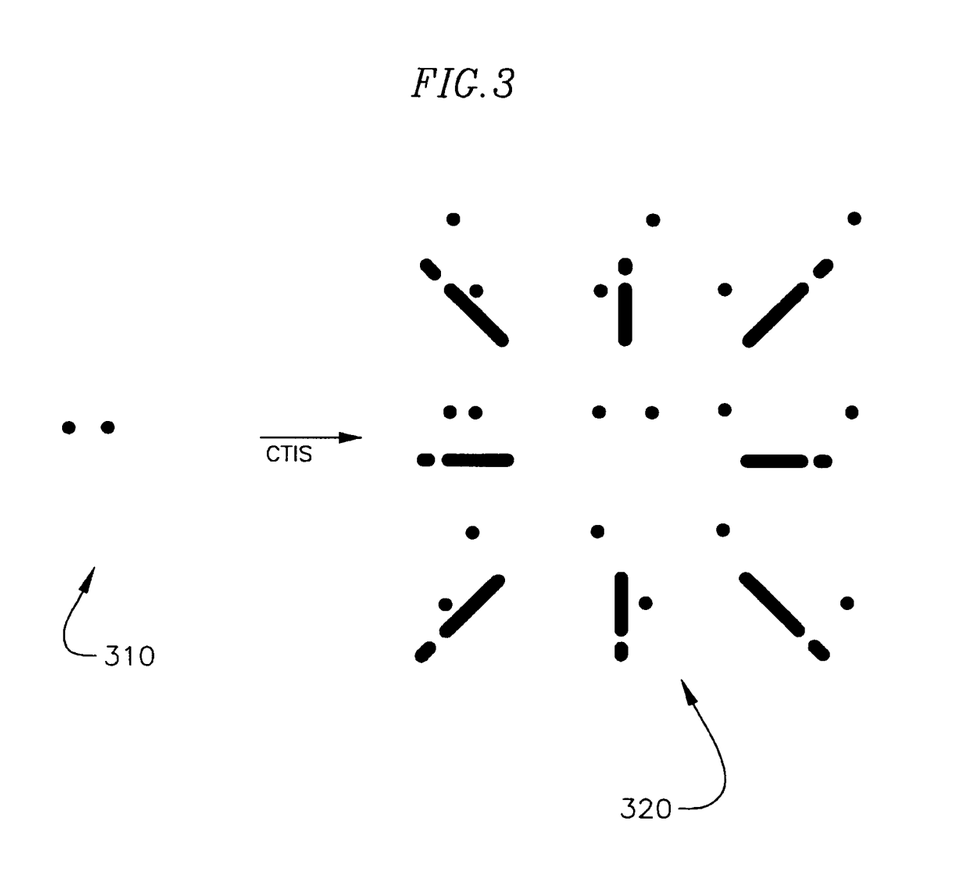
FIG. 3 is a field stop scene and a schematic depicting how the scene is dispersed by the CTIS system.

In operation, a primary optical system (e.g., a telescope, microscope, endoscope, etc.) forms a real image of the scene 310 on a field stop 131 serving as an aperture (as shown in FIG. 3). Light passing through the field stop 131 is filtered through a filter 133 and passed through the 2D grating 134, which produces a 2D array of diffraction orders 135. The lens 140 then images the diffraction orders of light 137 onto the FPA detector 138, which records the intensity of the incident light. An example of the diffraction orders of light 320, as imaged on the FPA detector 138 by the lens is shown in FIG. 3. Each diffraction order of light 137 transmitted from the 2D grating 134 produces a spectrally dispersed image of the scene, except for the undiffracted "zeroth" order which produces an undispersed image in the center of the FPA detector 138.

Reflective CTIS

Transmissive CTIS systems are not ideal for operation in the ultraviolet and infrared portions of the spectrum because there are few materials that transmit well. For this reason, the reflective CTIS has been developed. Typical reflective CTISs employ an Offner-type design, which is generally described in U.S. Pat. No. 6,522,403 to Wilson, et al., issued Feb. 18, 2003, the entire content of which is incorporated herein by reference.

Figure 4:
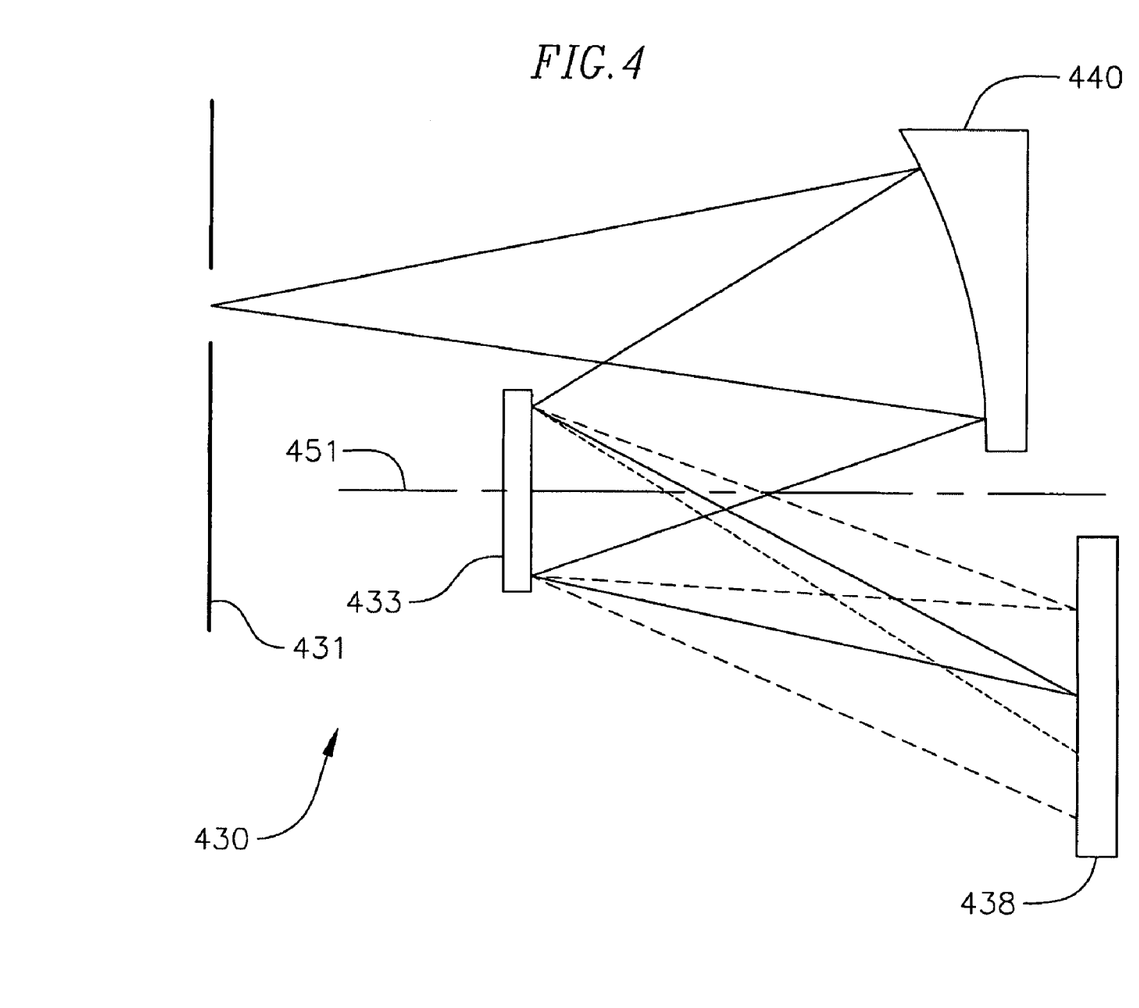
FIG. 4 is an optical layout of a CTIS system according to an alternative embodiment of the present invention.

In embodiments of the present invention, a modified Offner-type design is employed to reduce the weight and cost of the device. In one exemplary embodiment, as shown in FIG. 4, a reflective CTIS 430 according to embodiments of the present invention includes a 2D field stop aperture 431, a mirror 440, a 2D reflective diffraction grating 433 with a grating axis 451, and an FPA detector 438. The 2D field stop aperture may include any 2D aperture, including but not limited to squares, rectangles, circles, or ellipses, or arrays thereof. The plane of the field stop aperture 431 is approximately perpendicular to the grating axis 451.

Figure 5:
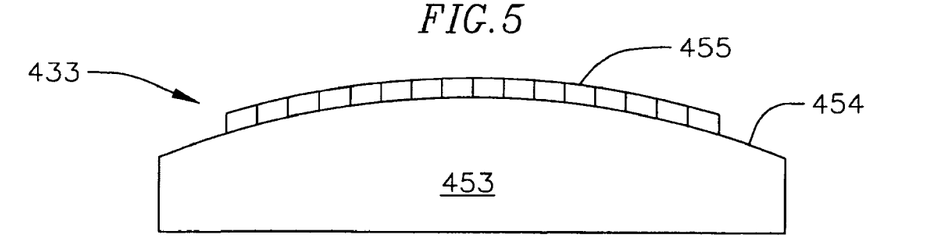
FIG. 5 is a schematic view of a grating according to an embodiment of the present invention.
Figure 6A:
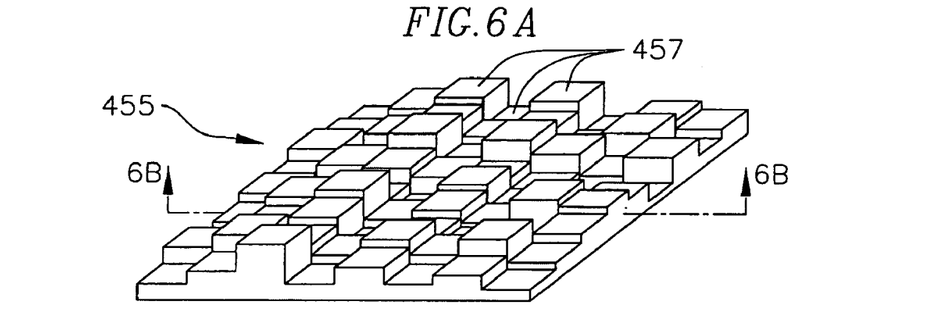
FIG. 6A is an enlarged view of the grating of FIG. 5.
Figure 6B:
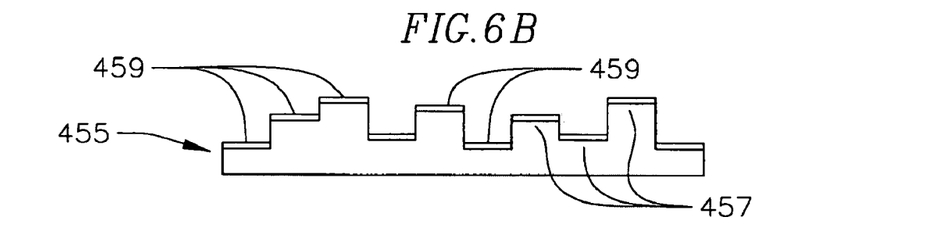
FIG. 6B is a cross-sectional view through line 6B-6B of the grating of FIG. 5 according to an embodiment of the present invention.
Figure 6C:
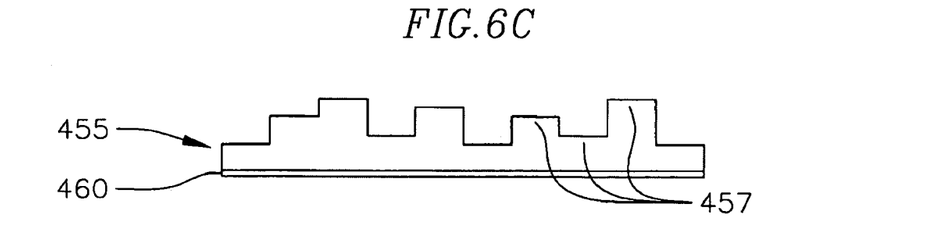
FIG. 6C is a cross-sectional view through line 6B-6B of the grating of FIG. 5 according to another embodiment of the present invention.

In one embodiment, the 2D reflective diffraction grating 433, which may be convex comprises a substrate 453 having a substrate surface 454 which supports a plurality of grating cells 455 as enlarged and illustrated in FIG. 5. Each grating cell 455 comprises an arrangement of a plurality of pixels 457 as greatly enlarged and illustrated in FIGS. 6A, 6B and 6C. The cells are identical to each other at least in a predetermined zone or area of the convex substrate surface 454. In one embodiment, the number of predetermined zones is about four. In another embodiment, the zones are arranged concentrically on the convex substrate surface 454. In FIG. 6A, the reflective surface 459 is on the top of pixels 457, whereas in FIG. 6C, the reflective surface 460 is on the bottom of pixels 457. In all embodiments, however, diffraction occurs as a result of the phase shift due to the varying heights of the pixels 457.

Figure 6D:
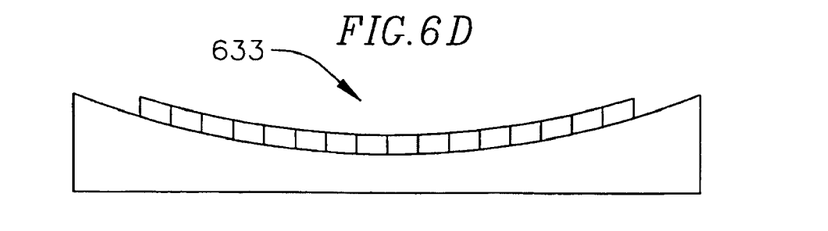
FIG. 6D is a schematic view of a grating according to another embodiment of the present invention.

In another embodiment of the invention, the 2D reflective diffraction grating 633 is concave, as shown in FIG. 6D. The reflective surface can be on the top or bottom of the cells as described with regard to FIGS. 6B and 6C. This particular grating can be used, for example, in the system shown in FIG. 4A, described in more detail below.

In one embodiment of the invention, a 2D computer-generated hologram ("CGH") grating is used as the diffraction grating. In one embodiment, the CGH grating is on a convex substrate instead of a one-dimensional blazed grating.

As shown in FIG. 4, in one embodiment, the mirror 440 is positioned to reflect light received from the field stop aperture 431 onto the diffraction grating 433, and the diffraction grating 433 is positioned to diffract and reflect the light onto the FPA detector 438. In this configuration, the mirror 440 is concave so that it reflects light back toward the diffraction grating 433, and the diffraction grating is convex so that it reflects light toward the FPA detector.

Figure 4A:
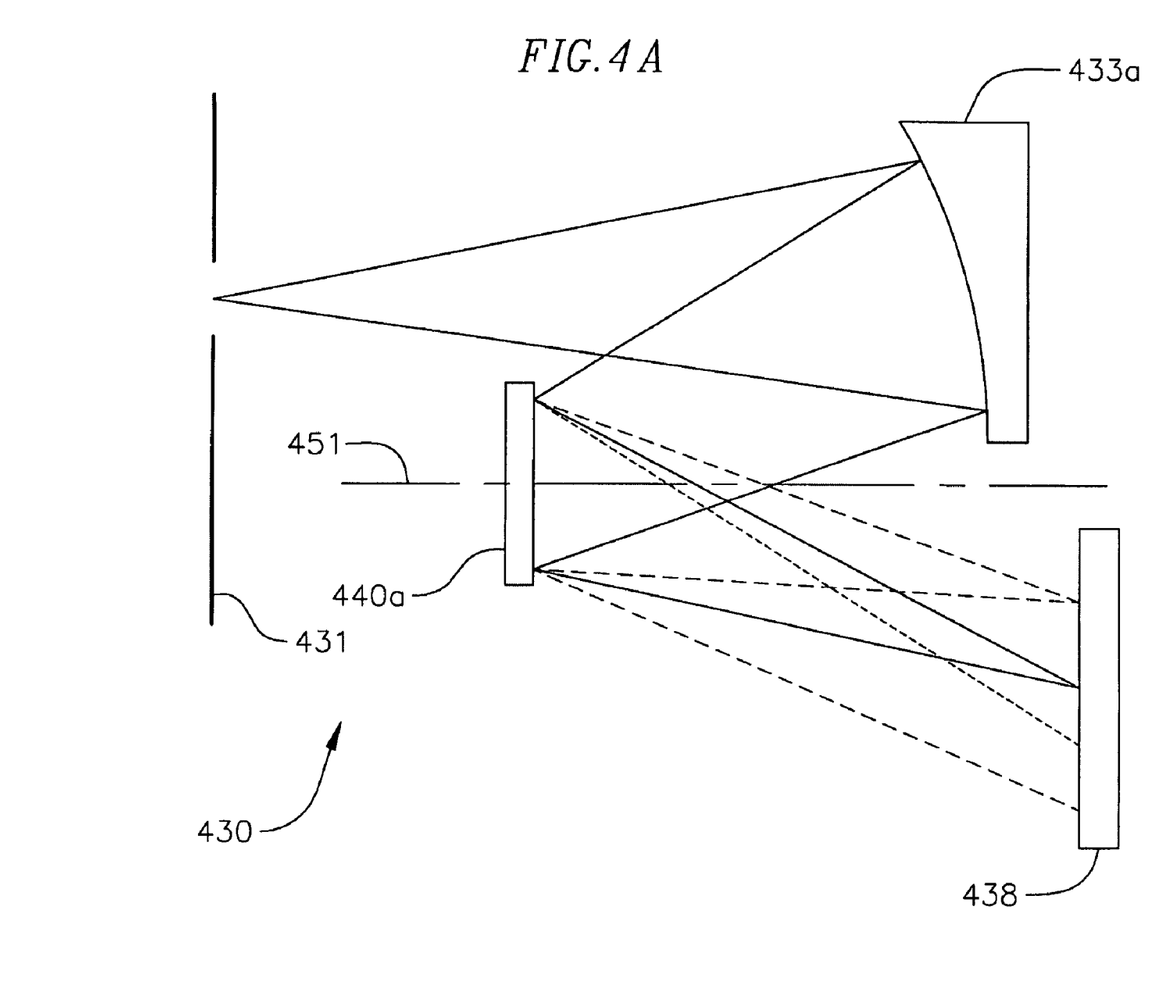
FIG. 4A is an optical layout of a CTIS system according to another embodiment of the present invention.

In an alternative configuration, as shown in FIG. 4A, the diffraction grating 433a is positioned to reflect light received from the field stop aperture 431 onto the mirror 440a, and the mirror 440a is positioned to reflect the light onto the FPA detector 438. In this configuration, the diffraction grating 433a may be concave so that is reflects the light toward the mirror 440a, and the mirror 440a may be convex so that it reflects light toward the FPA detector 438. However, although the grating 433a may be concave and the mirror 440a may be convex, it is understood that the grating 433a may take any geometry suitable to reflect the light toward the mirror 440a, and that the mirror 440a may take any geometry suitable to reflect the light toward the FPA detector.

The reflective CTIS 430 can be used in any spectrum. However, as noted above, reflective CTIS systems are particularly useful for operation in the infrared (IR) spectrum. Accordingly, in one embodiment, the FPA detector comprises an IR detector, for example a multiple wavelength IR detector.

Figure 7:
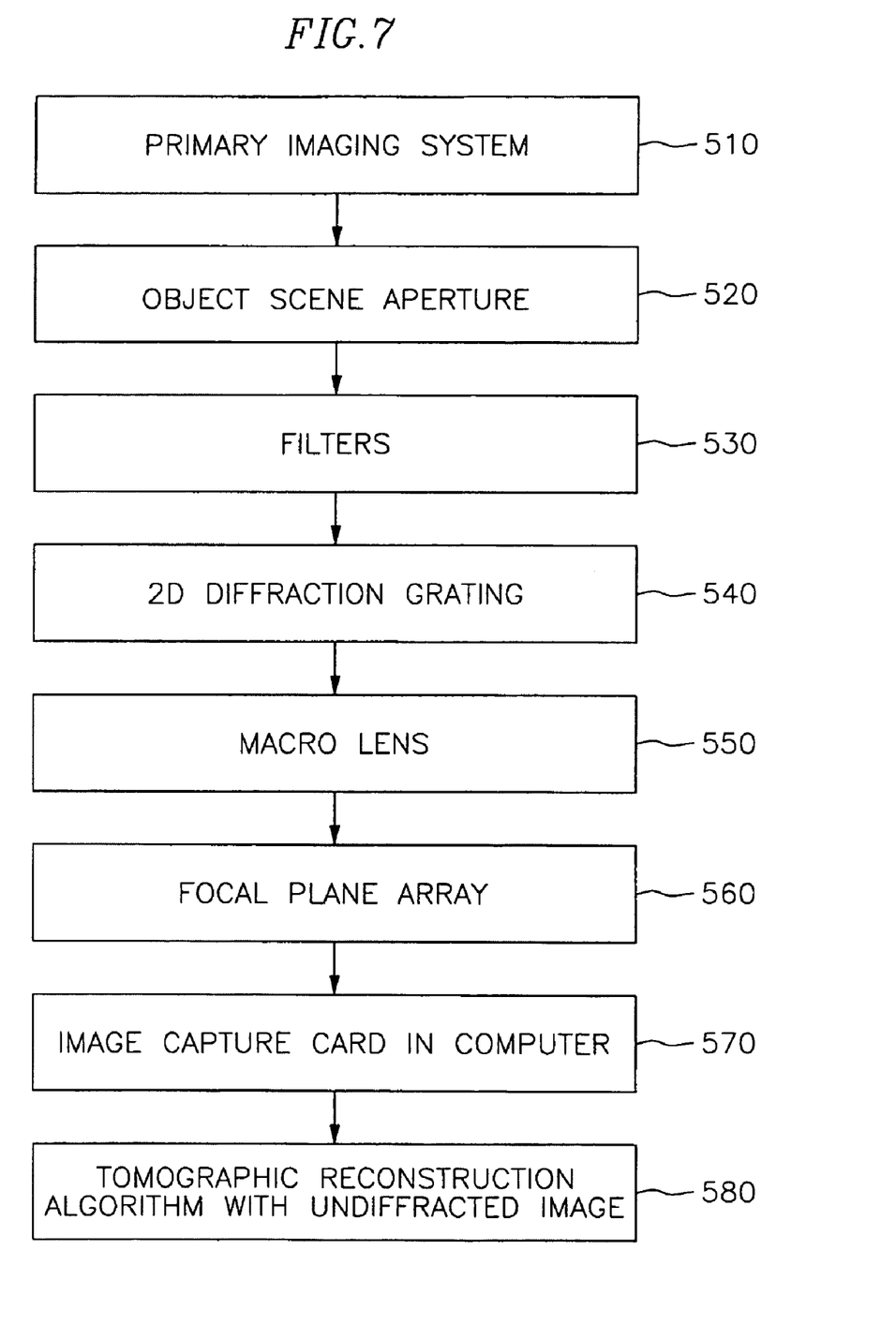
FIG. 7 is a flowchart of a method according to an embodiment of the present invention.

In another embodiment of the present invention, as shown in FIG. 7, a method of capturing spatial and spectral information includes providing radiation from a primary imaging system 510 incident upon an field stop aperture 520, and transmitting the radiation through at least one filter 530. The radiation is transmitted through the 2D diffraction grating 540, where it is diffracted. The radiation then passes through the lens 550, where it is focused onto a FPA detector 560 so that its intensity can be measured. A radiation associated signal is then transmitted from the FPA detector to an image capture card 570 in a computer where the signal is processed by a tomographic reconstruction algorithm 580. After a number of iterations, a data stream of spatial-spectral information from the object scene is produced.

Spectra Reconstruction and CTIS Calibration

An algorithm is used to reconstruct the spectra of all the points in the object scene from the captured intensity pattern and knowledge of how points and wavelengths in the field stop map to pixels on the detector. For reflective CTIS systems, spectra reconstruction, in one embodiment, may further include an undiffracted image constraint process. This process includes calculating the predicted undiffracted image based on the current estimate of the scene, then calculating a new set of scaling factors for the scene that force the predicted undiffracted image to equal the measured undiffracted image, and then uniformly scaling the entire scene so that the total number of photons in a predicted detector image remains constant from iteration to iteration.

However, prior to reconstructing the spectra of unknown scenes, the CTIS system must be calibrated. In a system using a monochrome camera as the FPA detector, light entering the field stop is polychromatic, yielding a three-dimensional input to the system, i.e. spatial dimensions x and y, and wavelength dimension $\lambda$. The three dimensional spatial-spectral volume is subdivided into small voxels. Calibration, then, is the determination of which detector pixels are illuminated by a given scene voxel and with what strength (i.e. "scene-voxel to detector-pixel mapping").

This scene-voxel to detector-pixel mapping is represented as a system matrix $H_{sys}$ that has $n_d$ rows and $n_s$ columns, where $n_d$ is the number of detector pixels and $n_s$ is the number of scene voxels. For any given scene $f_{scene}$ composed of voxels $s=1 \ldots n_s$, the detector image $g_{det}$ composed of pixels $d=1 \ldots n_d$ is given by Matrix Equation 1:

$$g_{det} = H_{sys} * f_{scene} \quad (1).$$

In Matrix Equation 1, $f_{scene}$ and $g_{det}$ are arranged as column vectors and all sources of noise have been ignored.

For a CTIS using a color camera as the FPA detector, the detector comprises three or more color images. Accordingly, the detector image $g_{det}$ is given by Matrix Equation 2:

$$[g_R; g_G; g_B] = [H_R; H_G; H_B] * f_{scene} \quad (2).$$

In Matrix Equation 2, R, G and B indicate the red, green and blue images, respectively. Matrix Equation 2 shows that there are three times the number of equations describing the color camera CTIS as for the monochrome CTIS. This means that the system is more "overdetermined" and better solutions for $f_{scene}$ can result.

To calibrate a monochrome camera system, a combination of measurements with numerical simulations is used. First, the efficiency of the system is measured at all wavelengths, and in all diffraction orders, but at only one spatial location in the field stop. This is done by placing a monochromatic-illuminated optical fiber in the center of the field stop, and recording detector images for many wavelengths in the spectral band of interest, e.g. 450-750 nm.

Each of these detector images is then computer analyzed to determine the efficiency, position, and aberrations, if severe, of each diffraction order at the given wavelength. This measurement includes the spectrally dependent transmission of all the optical elements and the responsivity of the color focal plane array detector.

With the system efficiency known, a simulation is used to derive the system transfer matrix H that maps voxels in the field stop to pixels on the detector. This is accomplished by tracing many rays from each voxel through the system, utilizing the measured information and keeping track of the resulting scene-voxel to detector-pixel connection weights. This simulation step can be replaced with actual measurements of scene-voxel to detector-pixel mappings by moving the fiber to each spatial location within the object scene plane. However, this increases the effort significantly and does not allow the voxel sizes (scene resolution) to be adjusted after calibration.

Once the system transfer matrix H is known, unknown scenes can then be imaged and their spectra reconstructed. An iterative expectation-maximization (EM) algorithm can be used, which algorithm was developed for reconstructing positron-emission tomography medical images. However, other known emission tomography algorithms can also be used.

Optical calibration of a color camera CTIS system would proceed in the same manner as calibration of monochrome CTIS systems, except that more attention is paid to the specific details of how the color camera FPA is implemented. As noted above, the monochrome camera technique involves using a monochromatic-illuminated fiber to measure the efficiencies, spot centroids, and point-spread functions for all diffraction orders at all wavelengths in the passband of the optical system. This information is then used in a ray-trace simulation to generate the system matrix of scene-voxel to detector-pixel interconnection strengths. The most straight-forward color FPA to calibrate would be the Foveon X3® direct image sensor because it uses three layers of pixels on top of one another, each sensitive to a different wavelength region (R, G or B), to measure the color component images. Because there is no spatial dependence of the color detection, no changes to the calibration scheme would be necessary.

On the other hand, most digital cameras in production today utilize Bayer color filter mosaics to measure the color incident on a 2×2 pixel region, with one red, two green, and one blue filter covering the pixels. Special demosaicing algorithms have been developed to derive the component color images from the filter mosaic images. When calibrating a Bayer FPA, the fiber used to calibrate the system should produce a point-spread function that is at least several 2×2 pixel regions in size to avoid individual filter effects.

The color FPA used for capturing the CTIS dispersed images enables each image pixel to return the fractions of red, green and blue of the incident light. This dramatically benefits CTIS reconstruction because the component color images exhibit more structure in response to even small changes in spectra compared to the monochrome image which is simply a weighted sum of the color images. This structure presents the reconstruction algorithm with the more difficult task of matching the predicted detector color images (generated by the spatial-spectral image cube) to the measured color detector images. Poor solutions are thus much more effectively rejected and reconstructions having more accurate spectra throughout the scene are obtained. In addition, when using a color FPA detector, using the zero order image as an initial guess gives better and faster results compared to black-and-white monochrome detectors, since the color already contains some spectral data.

Figure 8:
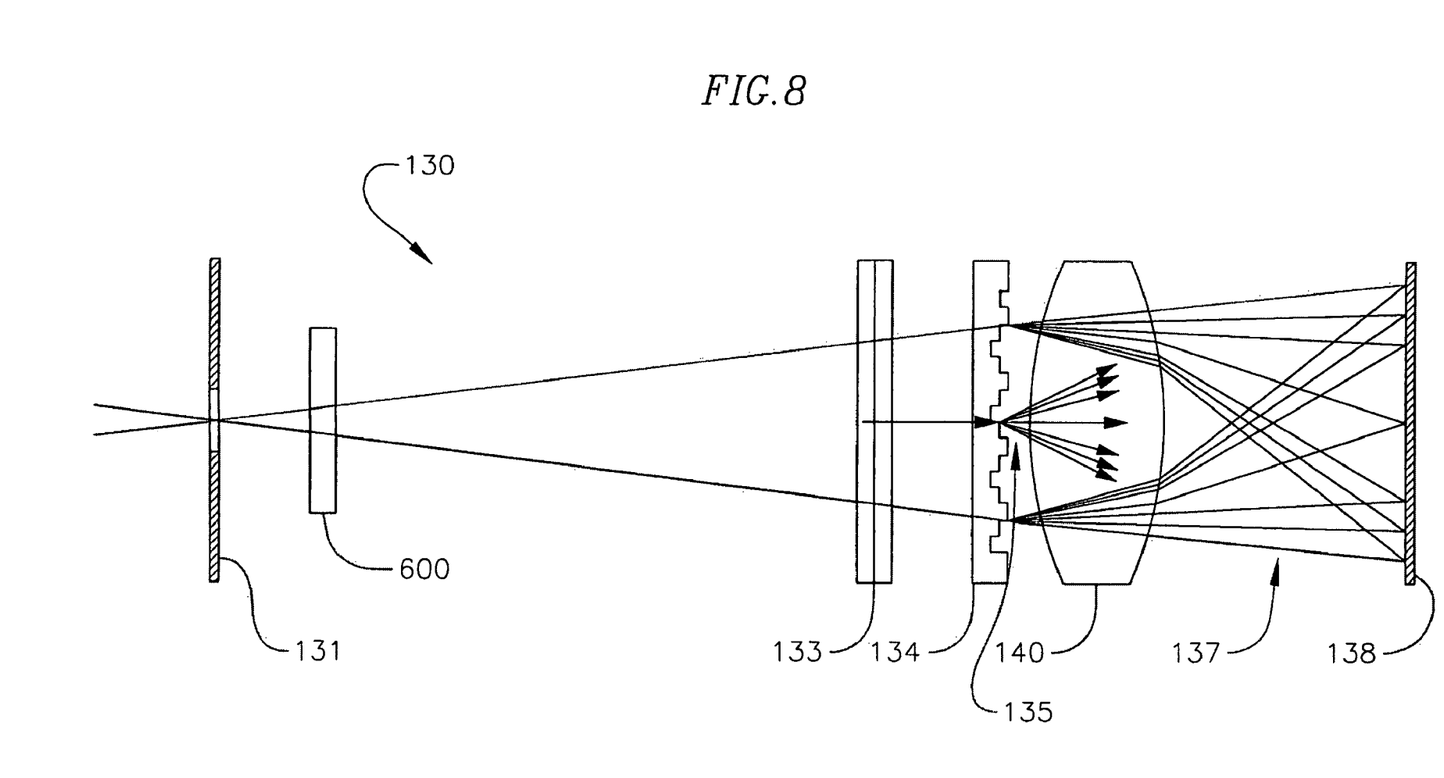
FIG. 8 is an optical layout of a CTIS system according to another embodiment of the present invention.
Figure 9:
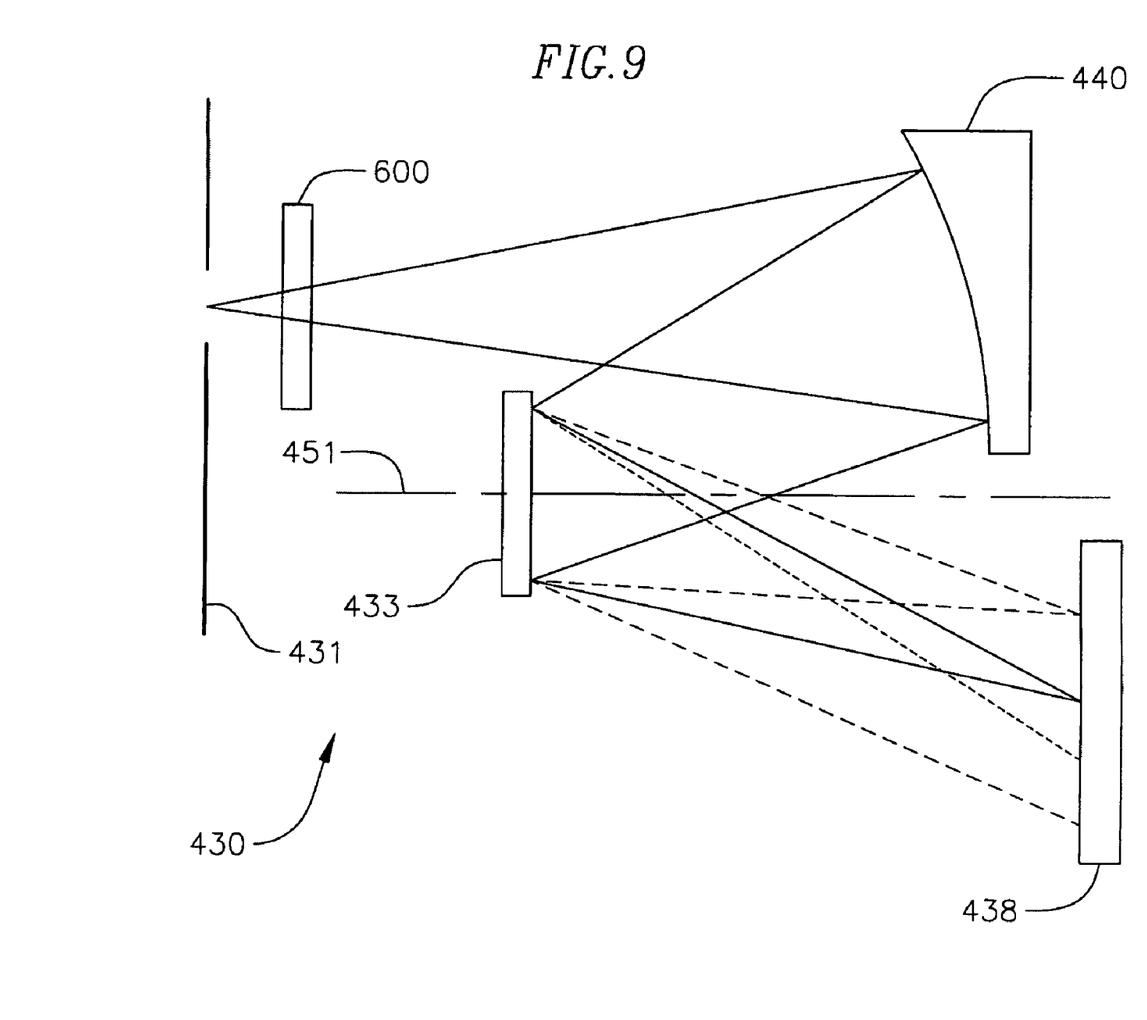
FIG. 9 is an optical layout of a CTIS system according to another embodiment of the present invention.

In some embodiment of the present invention utilizing color FPA detectors, as shown in FIGS. 8 and 9, the CTIS also includes artificial spatial structure imposed into the scene through the use of a pattern 600, for example a grid or checkerboard pattern. Such an imposition of spatial structure is described in detail in co-pending U.S. patent application titled "Spatial Image Modulation to Improve Performance of Computed Tomography Imaging Spectrometers," the entire content of which is incorporated herein by reference. In these embodiments, the extra structure imparted by the pattern 600 provides enough data for the algorithm to successfully recover the data. The spatial structure imposed may be provided either directly on the object being imaged (not shown) or at the aperture field stop, shown in FIG. 8 for a transmissive system and in FIG. 9 for a reflective system. The extra spatial information further improves the spectral reconstruction anywhere in the field.

According to these embodiments, spatial structure can be imposed in the image in a number of methods. For example, a digital multi-mirror device ("DMM") can be inserted at the field stop in a reflective CTIS (shown in FIG. 9). Any of the mirrors can be turned on or off to make any desired pattern. Alternatively, the spatial structure can be a reflective chrome mask on glass, provided at the field stop. In another alternative, the pattern could be projected onto the imaged object. A full image can be acquired by shifting the pattern with software for the DMM or by moving the mask. The same pattern can be imposed in a transmissive CTIS by placing an opaque mask at the aperture stop in FIG. 8.

In embodiments of the present invention, in which a single lens is used in place of the conventional collimation and re-imaging lenses, the positions of the dispersed images may change slightly due to the diverging wavefront incident on the grating. However, Fourier optics theory shows that a lens simply moves the Fourier transform of an object (the grating) from infinity to the focal position of the lens, with a known lateral scaling. In embodiments of the present invention employing a single lens, the lateral scaling factor may change, but the Fourier transform relationship holds and, hence, clearly focused dispersed images will be preserved. Therefore, the same quality of output information is obtained with the inventive CTISs as with conventional CTISs.

The preceding description has been presented with reference to certain exemplary embodiments of the present invention. However, workers skilled in the art and technology to which this invention pertains will appreciate that alterations and changes to the described embodiments may be practiced without meaningfully departing from the principal, spirit and scope of this invention. Accordingly, the foregoing description should not be read as pertaining only to the precise embodiments described and illustrated in the accompanying drawings, but rather should be read consistent with and as support for the following claims which are to have their fullest and fairest scope.

What is claimed is:

1. An imaging spectrometer for capturing spatial and spectral information from an object scene comprising:
   a focal plane array detector;
   a single lens configured to transmit and receive uncollimated light;
   a two-dimensional grating; and
   a field stop aperture.

2. The imaging spectrometer according to claim 1, wherein the single lens is configured to image the field stop aperture onto the focal plane array detector.

3. The imaging spectrometer according to claim 1, wherein the single lens comprises multiple glass elements.

4. The imaging spectrometer according to claim 1, wherein the single lens has an f-number of between about one and about two.

5. The imaging spectrometer according to claim 1, wherein the single lens is configured to receive the uncollimated light from the grating.

6. The imaging spectrometer according to claim 1, wherein the single lens is configured to transmit the uncollimated light to the grating.

7. The imaging spectrometer according to claim 1, wherein the focal plane array detector is a color focal plane array detector.

8. An imaging spectrometer for capturing spatial and spectral information from an object scene comprising:
   a focal plane array detector;
   a two-dimensional grating;
   a single mirror configured to reflect and receive uncollimated light; and
   a field stop aperture.

9. The imaging spectrometer according to claim 8, wherein the focal plane array detector is a color focal plane array detector.

10. The imaging spectrometer according to claim 8, wherein the mirror has an f-number of between about one and about two.

11. The imaging spectrometer according to claim 8, wherein the mirror is configured to focus uncollimated light onto the focal plane array detector.

12. The imaging spectrometer according to claim 8, wherein the mirror is configured to reflect the uncollimated light to the two-dimensional grating, and wherein the two-dimensional grating is configured to reflect the uncollimated light on the focal plane array detector.

13. The imaging spectrometer according to claim 8, wherein the two-dimensional grating is configured to reflect the uncollimated light to the mirror, and wherein the mirror is configured to reflect the uncollimated light on the focal plane array detector.

14. A method of capturing spatial and spectral information from an object scene, the method comprising:
   forming an image of the object scene on a field stop aperture;
   passing uncollimated light through the field stop aperture;
   dispersing the uncollimated light with a two-dimensional grating, wherein the two-dimensional grating produces a two dimensional array of uncollimated diffraction orders of light;
   focusing the uncollimated diffraction orders of light onto a focal plane array detector using a single lens or mirror; and
   recording the intensity of the light incident on the focal plane array detector.

15. The method according to claim 14, wherein the single lens or mirror is configured to image the field stop aperture onto the focal plane array detector.

16. The method according to claim 14, wherein the focal plane array detector is a color focal plane array detector.

17. A method of capturing spatial and spectral information from an object scene, the method comprising:
   forming an image of the object scene on a field stop aperture;
   passing uncollimated light through the field stop aperture to a single lens or mirror;
   passing the uncollimated light from the single lens or mirror to a two-dimensional grating;
   dispersing the uncollimated light with the two-dimensional grating, wherein the two-dimensional grating produces a two dimensional array of uncollimated diffraction orders of light and passes the uncollimated diffraction orders of light onto a focal plane array detector; and
   recording the intensity of the light incident on the focal plane array detector.

18. The method according to claim 17, wherein the focal plane array detector is a color focal plane array detector.

19. The method according to claim 17, wherein the single lens or mirror is configured to image the field stop aperture onto the focal plane array detector.

* * * * *